United States Patent [19]

Day

[11] Patent Number: 5,276,927
[45] Date of Patent: Jan. 11, 1994

[54] RADIOLUCENT HEAD SUPPORT

[75] Inventor: James L. Day, Cincinnati, Ohio

[73] Assignee: Ohio Medical Instrument Co., Fairfax, Ohio

[21] Appl. No.: 948,135

[22] Filed: Sep. 21, 1992

[51] Int. Cl.⁵ .................. A61G 13/12; A61G 13/10
[52] U.S. Cl. .......................... 5/622; 5/601; 5/637
[58] Field of Search ............ 5/622, 601, 637, 636, 5/640; 378/180, 208, 209; 297/406, 408

[56] References Cited

U.S. PATENT DOCUMENTS

| | | | |
|---|---|---|---|
| 3,099,441 | 7/1963 | Ries | 5/637 |
| 3,188,079 | 6/1965 | Boetcker et al. | 5/622 |
| 3,732,863 | 5/1973 | Harrington | 5/622 |
| 4,108,426 | 8/1978 | Lindstroem et al. | 5/637 |
| 4,169,478 | 10/1979 | Hickman | 5/637 |
| 4,545,572 | 10/1985 | Day | 5/637 |
| 4,779,858 | 10/1988 | Saussereau | 5/601 |

*Primary Examiner*—Alexander Grosz
*Attorney, Agent, or Firm*—Wood, Herron & Evans

[57] ABSTRACT

A head support for a patient support table having a skull securing clamp that is mounted to a non-circular support bar for selective attachment to the side rails of the patient support table. The skull clamp includes a non-circular support aperture for receiving the non-circular support bar. The structural components of the head support are made from radiolucent material and the support bar includes mounting posts at its first and second ends so that arms for mounting the support bar to the side rails may be located out of the path of the x-rays through the patient's head. The non-circular shape of the support aperture and the support bar prevent inadvertent rotation of the radiolucent skull securing clamp with respect to the radiolucent support bar. The location of the mounting posts on the support arms and the utilization of the radiolucent material results in fewer artifacts in the developed x-ray picture.

13 Claims, 2 Drawing Sheets

RADIOLUCENT HEAD SUPPORT

FIELD OF THE INVENTION

This invention relates to radiological equipment and, more particularly, radiological equipment used in neurological radiography.

BACKGROUND OF THE INVENTION

Supports for securing the head of a patient for surgical or radiological procedures are known in the art. The supports are typically adjustable so the head of the patient may be secured in different positions for different radiological views or to facilitate access to a patient's head during a surgical procedure. Such head supports typically include a support beam adapted to be mounted outward from one end of a patient support table, a head clamp, and one or more intervening adjusting members for adjusting the height and orientation of the head clamp with respect to the table. Such head supports are disclosed in U.S. Pat. Nos. 4,545,572 and 4,169,478 which are assigned to the assignee of the present application and commercialized by Ohio Medical Instrument Company, Inc. as the Mayfield TM Headrest.

The components of such head supports have usually been fabricated from stainless steel or other metals. One problem with head supports comprised of metal components is that the metal is radiopaque to x-rays which produces "artifacts" in the x-rays taken when the headrest is interposed between the x-ray source and the x-ray film. These artifacts are created by the metal head support components blocking the path of the x-rays as they travel from the source to the film. The areas of the x-ray film that remain unexposed because the x-rays are blocked by the head support appear as artifacts in the developed x-ray picture. These artifacts diminish the usefulness of the developed x-ray picture because they obscure the image of a portion of the head that normally would be viewable, absent the obscuring head support component.

The use of radiolucent materials which permit x-rays to pass through them have been used in known head supports to reduce artifacts. While the x-ray pictures produced by using these head supports have fewer artifacts, they present other problems to the radiologist. Specifically, most known head supports are mounted to one end of the patient support table at or near the center of the table's width with mounting rails. The mounting rails are made from radiopaque materials because the radiolucent materials are not sufficiently strong enough to rigidly hold the head support. While the radiolucent material of the head support components permits most of the x-rays to pass through, the mounting rails do block part of the x-rays which results in a smaller artifact but one which can obscure finer details in a developed x-ray picture. What is needed is a way of reducing the number of headrest components that are interposed between the x-ray source and the x-ray film.

Another problem with previously radiolucent head supports is the difficulty of mating an adjustable head support made from a radiolucent material to another component made of radiolucent material so the two components do not slip relative to one another under the pressure exerted by the patient's head. Slippage occurs because the surfaces of the radiolucent material have lower coefficients of friction than those of the metal surfaces in previously known head supports. While circumferential collars and grooved surfaces have been previously used, they require machining and the incorporation of tightening devices such as threaded bolts and apertures. What is needed is a simple way to maintain a mating relationship between head support components made from radiolucent materials.

SUMMARY OF THE INVENTION

To solve the above identified problems, a head support built in accordance with the principles of the present invention includes an adjustable skull clamp and a non-circular support bar made of radiolucent material so the skull clamp may be non-rotatably mounted to the support bar. Preferably, a securing screw is provided to bias the skull clamp into the non-rotatable mounting relationship with the support bar. Most preferably, the support bar is a non-circular solid having cylindrical mounting posts at its first and second ends and the skull clamp includes a non-circular aperture for snugly receiving the support bar intermediate the mounting post.

The head support built in accordance with the principles of the present invention may be mounted to the side rails of a patient support table to remove the table mounting rails from the path of the x-rays as they pass through the patient's head to the x-ray film. The novel non-circular shape of the support bar and the aperture in the skull clamp prevents rotational movement of the skull clamp with respect to the support bar. The cylindrical posts mounted at the first and second ends of the support bar permit pivotal movement of the support in conventional mounting members that attach the support bar to the side rails of the patient support table. The head support of the present invention provides secure engagement of the skull clamp with the support bar so the position of the patient's head does not change during the taking of an x-ray and the developed x-ray picture contains fewer artifacts since the cylindrical posts at the first and second ends permit the support bar to be mounted to the side rails of the table and not at the center of the table width.

These and other novel aspects and advantages of the present invention shall be made apparent from the accompanying drawings and the description thereof.

DESCRIPTION OF THE DRAWINGS

The accompanying drawings, which are incorporated in and constitute a part of the specification, illustrate a preferred embodiment of the invention and, together with the general description given above and the detailed description given below serve to explain the principles of the invention.

DETAILED DESCRIPTION OF THE INVENTION

Figure 1:
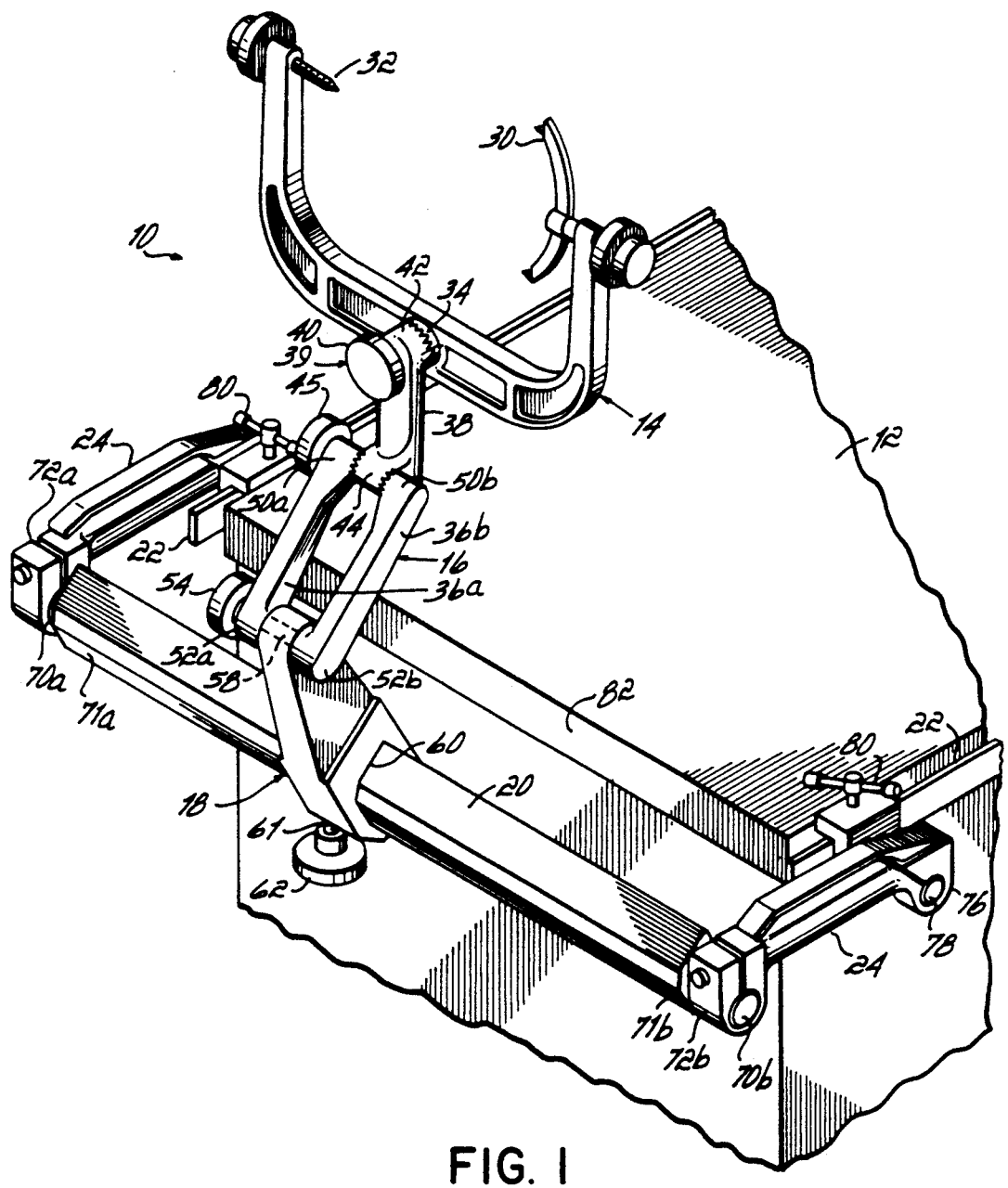
FIG. 1 is fragmentary perspective view of a preferred embodiment of the head support, as mounted to a patient support table.

A head support 10 built in accordance with the principles of the present invention is shown in FIG. 1. Head support 10 is mounted to a patient support table 12 at one end of the table in a manner to be discussed in more detail below. The head support 10 includes a skull clamp 14, an adjustable bracket 16, a mounting member 18, and a support bar 20. Support bar 20 is mounted to side rails 22 by mounting arms 24, 24 at each end. Most preferably, the major structural members of skull clamp 14, adjustable bracket 16, mounting member 18, and support bar 20 are made from a carbon composite material preferably comprised of polyethersulfone (PES) and carbon with the carbon component being 30% of the composite by weight. Such a material is available from ICI Advanced Materials of Exton, Pa. under the commercial name THERMOCOMP JC-1006 or from LNP Engineering Plastics, Inc. of Thorndale, Pa. under the commercial name STAT-KON JC-1006. Alternatively, the skull clamp 14 and adjustable bracket 16 may be made with the carbon composite material and the mounting member 18 and the support bar 20 may be made from a radiolucent plastic such as acetal. (Minor structural elements such as springs, pins or the like not directly in the path of the x-rays (FIG. 2) may be made of metal but it is desirable to eliminate the use of metal to the greatest extent possible.)

In more detail, the head support 10 of FIG. 1 includes a U-shaped skull clamp 14 having a cradle 30 and a screw 32 mounted at opposite ends of the clamp 14. Screw 32 and cradle 30 cooperate to secure a patient's head in a fixed position in a conventionally known manner. Intermediate the ends of the U-shaped clamp 14 is a mounting collar 34 having V-grooves cut in the collar and also having a screw receiving aperture (not shown) concentric with the collar 34 for mounting the U-shaped clamp 14 to adjustable member 16.

Adjustable member 16 includes a pair of pivotable mounting arms 36a, 36b and a mounting post 38. At one end of mounting post 38 is a bore (not shown) through which an adjusting screw 39 is received. The adjusting screw 39 has a knob 40 mounted at one end so the adjusting screw 39 may be selectively tightened and loosened within the threaded aperture. Opposite the knob 40 is a mounting collar 42 having V-grooves that mate with the V-grooves of mounting collar 34 on skull clamp 14. By rotating knob 40 so the adjusting screw 39 is advanced through the aperture in post 38 and the aperture within mounting collar 34, the skull clamp 14 is fixedly mounted to the mounting post 38. The orientation of the skull clamp may be changed with respect to mounting post 38 by loosening the adjusting screw with the knob 40, rotating the mounting collar 34 with respect to mounting collar 42 and then re-tightening the screw 39 to hold the mounting collars in engagement with one another. At its other end, mounting post 38 includes a mounting cylinder 44 having V-grooves at each end of the cylinder and a passageway through the cylinder for receiving a mounting bolt having a knob 45.

Adjustment arms 36a, 36b have V-groove collars 50a, 50b at one end and mounting receptacles 52a, 52b at the other end. A mounting bolt having a knob 54 at one end passes through receptacle 52a of adjusting arm 36a and into receptacle 52b of adjusting arm 36b. The receptacle 52b is threaded so the adjusting bolt can be tightened by rotating knob 54.

Figure 3:
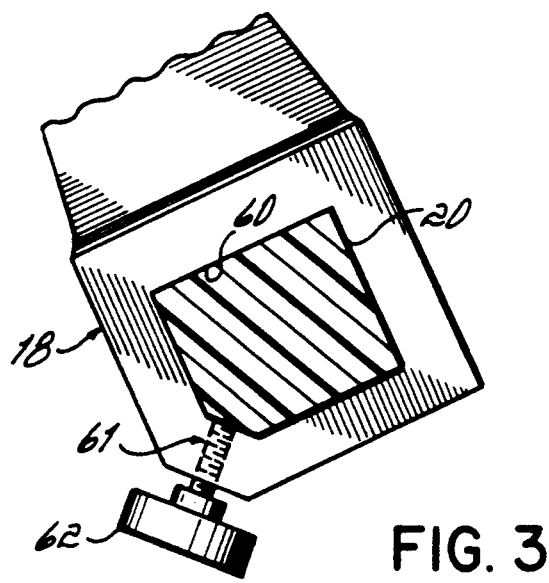
FIG. 3 is a partial cross-sectional view of the support bar and the mounting member of the present invention, taken on line 3—3 of FIG. 2.

Mounting bracket 18 includes an aperture 58 at one end that is interposed and mated with the receptacles 52a, 52b of adjusting arms 36a, 36b, respectively. Placing the mounting bolt so it extends through the receptacles 52a, 52b and aperture 58 in mounting bracket 18 permits adjustable bracket 16 to be connected to the mounting bracket 18. Because adjustable bracket 16 may be rotated when knob 54 is turned to loosen the mounting bolt within receptable 52b, the vertical displacement of the head support 10 from the patient support table 12 may be selectively adjusted. The other end of mounting bracket 18 includes a support aperture 60 that is configured in the same non-circular shape as support bar 20 and sized to snugly receive the support bar 20 (FIG. 3). Mounting bracket 18 also includes a locking or set screw 61 having a knob 62 that may be used to selectively tighten the screw against a side of the support bar 20.

Support bar 20 has a non-circular cross-section that mates with support aperture 60 of mounting bracket 18. Mounting bracket 18 may be moved intermediate the ends of support bar 20 to vary the horizontal displacement of the head support 10 within the width of the patient support table 12 and the selected horizontal position may be secured by screw 61. The mating of the non-circular support aperture 60 and the non-circular support bar 20 prevents rotational slippage between the mounting bracket 18 and the support bar 20 relative to one another while screw 61 set by knob 62 prevents horizontal displacement of the mounting bracket 18. In previously known head supports using radiolucent materials, securement of a cylindrical support bar within a cylindrical support aperture in a mounting bracket could not be maintained—even with a set screw. This is thought to arise from the low coefficient of friction of the two carbon composite surfaces. This rotational slippage problem is substantially reduced by the novel non-circular cross-section of the support bar 20 and support aperture 60 made according to the principles of the present invention.

The mounting bracket 18 and support bar 20 of the present invention also permit horizontal adjustment of the head support along substantially the entire width of the support table 12 and removes the mounting arms 24 for mounting the support bar to the table 12 from the area underneath the skull clamp 14. The removal of the mounting arms 24 from this area results in fewer artifacts being produced by the head support components in the developed x-ray picture.

Mounting posts 70a, 70b extend from ends 71a, 71b of support bar 20, respectively. The mounting posts 70a, 70b are sized to fit within mounting collars 72a, 72b located at one end of each mounting arm 24. The mounting collars 72a, 72b are made of metal and therefore grip the mounting posts 70a, 70b sufficiently to prevent their inadvertent rotation within the mounting collars 72a, 72b. The other end of each mounting arm 24 includes a second mounting collar 76 which receives a mounting post 78 that extends from an adjustable table mount 80. The mount 80 is slidably mounted on side rail 22. This arrangement provides for adjusting the horizontal separation between support bar 20 and end 82 of table 12.

Figure 2:
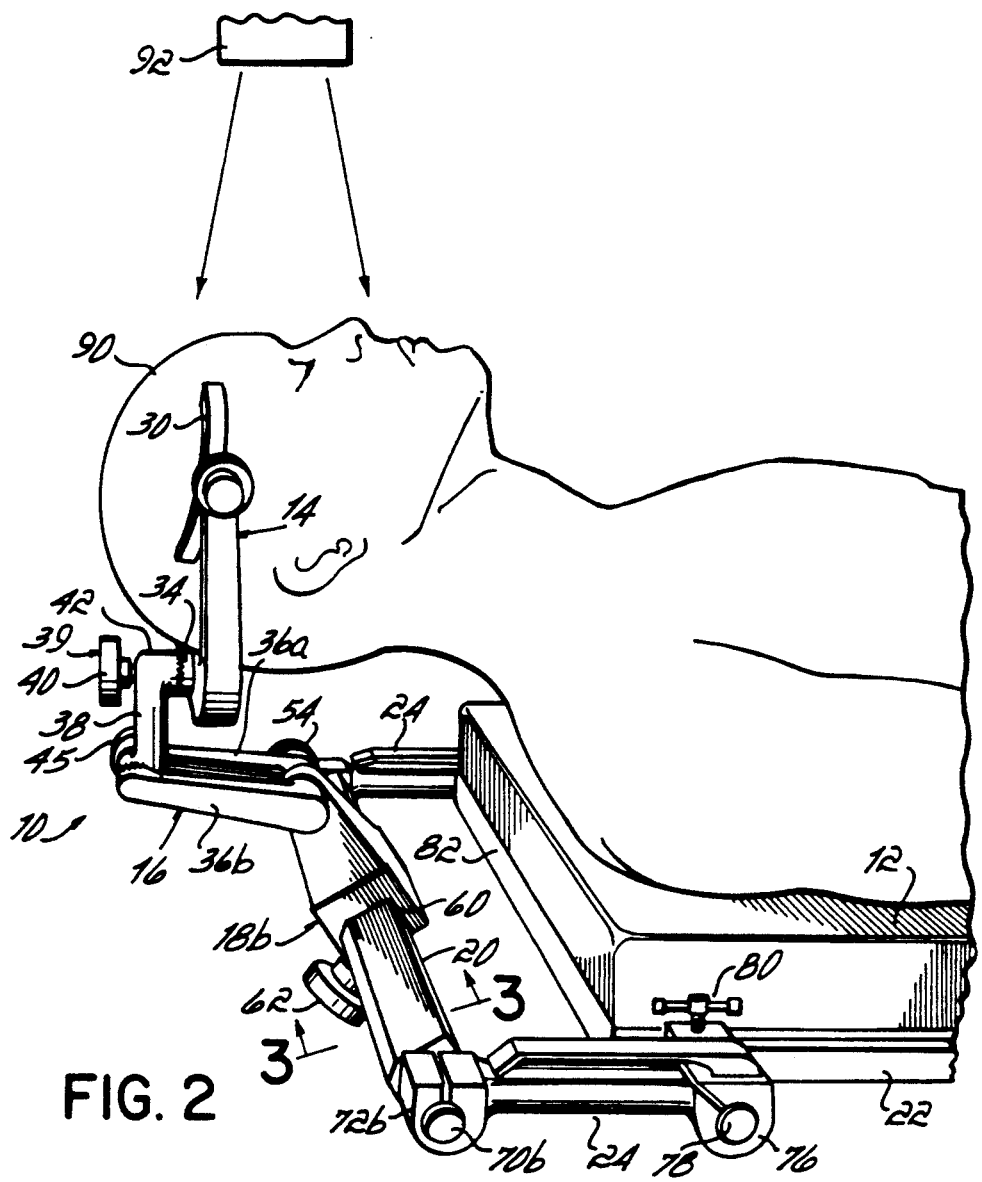
FIG. 2 is a diagrammatic perspective view of a patient's head secured within the support of FIG. 1, during an x-ray exposure thereof.

As shown in FIG. 2, the head support 10 can be used to secure the head 90 of a patient in a desired, fixed relationship to an x-ray source 92. Cradle 30 may be rotated for rotational adjustment of the head within U-clamp 14 and the patient's head 90 can be secured within the clamp 14 at the desired position. Likewise, knobs 40, 45, and 54 may be used to further adjust the vertical and horizontal displacement of the patient's head with respect to the patient support table 12. Further horizontal adjustment with respect to support table 12 is provided through the release and tightening of locking screw 61 in support aperture 60 for the horizontal movement of mounting bracket 18 of support bar 20. As evident in FIG. 2, the head support 10 securely holds the patient's head without significant slippage between radiolucent components of the head support and without interposing the radiopaque mounting arms 24 between the x-ray source 92 and the x-ray film (not shown) which is usually located below the head support 10.

While a preferred embodiment of the present invention has been described, further modifications and changes would be apparent to one of ordinary skill in the art without departing from the principles of the invention. It is intended that all such changes and modifications obvious to one of ordinary skill in the art be covered by the appended claims.

What is claimed is:

1. A head support for a patient support table comprising:
   means for selectively securing a patient's skull at a fixed position;
   means for supporting said skull securing means, said supporting means being non-circular in section so that said skull securing means may be non-rotatably mounted to said supporting means; and
   each of said skull securing means and said supporting means being made substantially from radiolucent material, said non-circular supporting means preventing slippage between said radiolucent skull securing means and said radiolucent supporting means so that a patient's skull secured in said skull securing means may be photographed by an x-ray source without producing artifacts in the resulting x-ray when the head support is interposed between the x-ray source and the x-ray film.

2. The head support of claim 1, said supporting means having first and second ends and further comprising:
   first and second mounting posts extending from said first and second ends of said supporting means whereby said supporting means may be mounted to said rails of a patient support table and the supporting means may be rotated with respect to said patient support table.

3. The support of claim 1 further comprising:
   means for adjusting the vertical and horizontal position of said skull securing means with respect to said supporting means.

4. The head support of claim 1 wherein said skull securing means slidably receives said supporting means.

5. The head support of claim 1 further comprising:
   means for fixing the position of said skull securing means along a length of said non-circular supporting means.

6. The head support of claim 5 wherein said position fixing means extends through said skull securing means and bears against a side of said non-circular supporting means.

7. A surgical head support adapted to be adjustably connected to a patient support table, comprising:
   a head clamp having first and second ends and a collar intermediate said first and second ends;
   a vertical post having first and second ends, said first end being adapted to mate with said collar so that said head clamp may be selectively rotated and secured in a first vertical plane;
   a height adjusting member having first and second ends, said first end being adapted to mate with said second end of said vertical post so that said vertical post may be rotated and secured in a second vertical plane perpendicular to said first vertical plane;
   a sliding member having first and second ends, said first end being adapted to pivotally mate with said second end of said height adjusting member so that said height adjusting member may be pivoted and secured in said second vertical plane to vary the height of said head clamp with respect to the table;
   a support bar having first and second ends that terminate at each end into a mounting post, said support bar extending through said second end of said sliding member so that said sliding member may be selectively positioned and secured along said support member between said first and second ends of said support member, each of said mounting posts being adapted to be received in a mounting arm connected to the patient support table so the support bar may be selectively rotated in said second vertical plane; and
   said head clamp, said vertical post, said height adjusting member, said sliding member, and said support bar being substantially made from a radiolucent material whereby x-ray pictures taken of a head secured in said head clamp are free of artifacts.

8. The support of claim 7, said radiolucent material being a carbon composite having at least 30% carbon by weight.

9. The head support of claim 8, said carbon composite further includes polyethersulfone.

10. The head support of claim 7, wherein said head clamp, said vertical post and said height adjusting member being made from a carbon composite material; and
    said sliding member and said support bar being made from a radiolucent plastic.

11. The head support of claim 10 wherein said carbon composite material having approximately 30% carbon by weight.

12. The head support of claim 11 wherein said carbon composite material further includes polyethersulfone.

13. The head support of claim 12 wherein said mounting posts are rotatable in metal collars for rotation relative to said table.

* * * * *

UNITED STATES PATENT AND TRADEMARK OFFICE
CERTIFICATE OF CORRECTION

PATENT NO. : 5,276,927
DATED : January 11, 1994
INVENTOR(S) : James L. Day

It is certified that error appears in the above-indentified patent and that said Letters Patent is hereby corrected as shown below:

Col. 5, line 21, after "position" insert --relative to the support table, said securing means having a support aperture that is noncircular in section--.

Col. 5, line 22, before "means for" insert --elongated support bar--.

Col. 5, line 24, after "said" insert --support aperture of said--.

Col. 5, line 27, after "from" insert --slippery nonmetallic--.

Col. 6, line 28, change "member" to --bar--.

Signed and Sealed this

Twenty-first Day of October 1997

Attest:

BRUCE LEHMAN

*Attesting Officer*   *Commissioner of Patents and Trademarks*